United States Patent
Simpson et al.

(10) Patent No.: US 10,369,343 B2
(45) Date of Patent: Aug. 6, 2019

(54) APPARATUS AND METHOD TO CONVEY A FLUID

(75) Inventors: Thomas J. Simpson, Surrey (GB); Jim Hagerman, Surrey (GB)

(73) Assignee: Biocompatibles UK Limited, Farnham, Surrey (GB)

( * ) Notice: Subject to any disclaimer, the term of this patent is extended or adjusted under 35 U.S.C. 154(b) by 843 days.

(21) Appl. No.: 11/479,274

(22) Filed: Jun. 30, 2006

(65) Prior Publication Data

US 2008/0004599 A1    Jan. 3, 2008

(51) Int. Cl.
*A61M 37/00* (2006.01)
*A61M 5/14* (2006.01)
*A61N 5/10* (2006.01)

(52) U.S. Cl.
CPC .......... *A61M 37/0069* (2013.01); *A61M 5/14* (2013.01); *A61M 2206/14* (2013.01); *A61M 2206/20* (2013.01); *A61N 5/1001* (2013.01)

(58) Field of Classification Search
CPC ...... A61M 2039/0264; A61M 2206/14; A61M 5/14; A61M 25/0097; A61M 37/0069; A61M 39/10; A61M 39/105; A61M 2206/20
USPC ......... 604/246, 247, 48, 533, 534, 535, 537, 604/538, 539, 905, 93.01
See application file for complete search history.

(56) References Cited

U.S. PATENT DOCUMENTS

| | | | | |
|---|---|---|---|---|
| 4,429,856 A | * | 2/1984 | Jackson | A61M 16/04 137/843 |
| 4,674,480 A | | 6/1987 | Lemelson | |
| 5,242,393 A | * | 9/1993 | Brimhall | A61M 39/26 604/249 |
| 5,660,205 A | * | 8/1997 | Epstein | 137/512.15 |
| 5,817,069 A | * | 10/1998 | Arnett | A61M 39/26 251/149.1 |
| 6,165,168 A | * | 12/2000 | Russo | 604/533 |
| 6,306,366 B1 | | 10/2001 | Heldmann et al. | |
| 6,343,603 B1 | * | 2/2002 | Tuck | A61M 16/08 128/204.18 |
| 6,709,427 B1 | * | 3/2004 | Nash | A61B 17/32037 604/508 |
| 7,344,491 B1 | | 3/2008 | Seeney et al. | |
| 2002/0084290 A1 | * | 7/2002 | Materna | B01L 3/0241 222/420 |
| 2002/0197211 A1 | | 12/2002 | Henriksen et al. | |
| 2003/0013951 A1 | | 1/2003 | Stefanescu | |
| 2003/0135113 A1 | * | 7/2003 | Altman et al. | 600/431 |

(Continued)

FOREIGN PATENT DOCUMENTS

| | | |
|---|---|---|
| EP | 1035884 | 9/2000 |
| EP | 1069888 | 9/2004 |

(Continued)

OTHER PUBLICATIONS

PCT International Search Report; International App. No. PCT/IB2007/001780; dated Mar. 6, 2008.

(Continued)

*Primary Examiner* — Shefali D Patel
(74) *Attorney, Agent, or Firm* — Finnegan, Henderson, Farabow, Garrett & Dunner, L.L.P.

(57) ABSTRACT

An apparatus includes a fluid path, a coupling, and a nozzle. The fluid path is to carry a fluid including one or more microparticles. The coupling is located in the fluid path. The nozzle is located in the fluid path to move the fluid through a stagnant region located near the coupling.

10 Claims, 11 Drawing Sheets

(56) References Cited

U.S. PATENT DOCUMENTS

| | | | |
|---|---|---|---|
| 2003/0221561 A1* | 12/2003 | Milo | 96/175 |
| 2004/0002685 A1 | 1/2004 | Patzer | |
| 2004/0068157 A1 | 4/2004 | Gellman et al. | |
| 2004/0096511 A1 | 5/2004 | Harburn et al. | |
| 2004/0199141 A1 | 10/2004 | Altman | |
| 2004/0222144 A1 | 11/2004 | Nakatani et al. | |
| 2004/0258614 A1 | 12/2004 | Line | |
| 2005/0019257 A1 | 1/2005 | Kim et al. | |
| 2005/0020869 A1 | 1/2005 | Hainfeld et al. | |
| 2005/0087715 A1* | 4/2005 | Doyle | A61M 39/045 251/149.1 |
| 2005/0234431 A1 | 10/2005 | Williams et al. | |
| 2006/0089605 A1 | 4/2006 | Fitzgerald | |
| 2006/0129112 A1 | 6/2006 | Lynn | |
| 2006/0184140 A1 | 8/2006 | Okiyama | |
| 2007/0032775 A1 | 2/2007 | Niedospial et al. | |
| 2007/0083162 A1 | 4/2007 | O'Reagan et al. | |
| 2007/0156103 A1 | 7/2007 | Chatlynne et al. | |
| 2007/0260197 A1 | 11/2007 | Mick et al. | |
| 2008/0208052 A1 | 8/2008 | LePivert | |

FOREIGN PATENT DOCUMENTS

| | | |
|---|---|---|
| JP | 58-156776 | 9/1983 |
| JP | 04-054396 | 2/1992 |
| JP | 6-246668 | 9/1994 |
| JP | 6-246669 | 9/1994 |
| JP | 11-182751 | 7/1999 |
| JP | 2001-330185 | 11/2001 |
| JP | 2001-349483 | 12/2001 |
| JP | 2002-503991 A | 2/2002 |
| JP | 3118508 | 1/2006 |
| RU | 2137502 | 9/1999 |
| RU | 2207808 | 1/2003 |
| WO | WO 98/56435 | 12/1998 |
| WO | WO 2005/004973 A1 | 1/2005 |

OTHER PUBLICATIONS

Translation of an Office Action issued by the Russian Patent Office, dated Apr. 12, 2011, 7 pages.
Japanese Office Action for Japanese Patent Application No. 2009-517469, with English translation, 13 pages, dated May 21, 2012.
Japanese Office Action with English translation for corresponding Japanese App. No. 2009-517469, 13 pages, dated Apr. 5, 2013.
Japanese Office Action for Japanese Patent Application No. 2012-255119, with English translation, 5 pages, dated Oct. 29, 2013.
English language abstract of JP 2002-503991A, Feb. 5, 2002.

* cited by examiner

```
                    ┌─ BEGIN ─┐                    ←400
                          │
            ┌─────────────────────────────┐
            │  COUPLE A SOURCE OF HIGH    │
            │  DENSITY MICROPARTICLES     │──402
            │  HAVING HIGH SPECIFIC       │
            │  ACTIVITY TO A MAMMAL.      │
            └─────────────────────────────┘
                          │
            ┌─────────────────────────────┐
            │ DELIVER THE HIGH DENSITY    │
            │ MICROPARTICLES HAVING HIGH  │
            │ SPECIFIC ACTIVITY TO        │──404
            │ THE MAMMAL AT A PRESSURE OF │
            │ BETWEEN ABOUT 5 PSIG AND    │
            │ ABOUT 30 PSIG.              │
            └─────────────────────────────┘
                          │
                      ┌─ END ─┐
```

FIG. 4

SUMMARY TABLE

| Catheter Size (French) | Pressure Range (psig) | Equivalent Flow Rate (mL/s) | Flush Volume (mL) |
|---|---|---|---|
| 3 | 5-30 | 0.49±0.44 | <60 mL |
| 5 | 5-30 | 2.1±0.9 | <60 mL |

FIG. 5

APPARATUS AND METHOD TO CONVEY A FLUID

FIELD

The present invention relates to conveying a fluid, and more particularly, to conveying a fluid that includes microparticles.

BACKGROUND

In some systems, such as therapeutic systems employed in the treatment of disease, a fluid is conveyed or delivered to a target, such as a cancerous tumor, through a conduit that includes a coupling. For a fluid that includes microparticles, such as radioactive microparticles or radioactive microspheres, the microparticles can become trapped at the coupling.

Some microparticles are trapped in gaps that result from mechanically mismatched components in the coupling. Other microparticles are trapped in regions of stagnant fluid flow, such as regions in which the fluid velocity is less than the saltation velocity. Corners and discontinuities in the coupling can create regions of fluid expansion in which the fluid velocity is less than the saltation velocity. A force field, such as gravity, can also contribute to the trapping of microparticles. In some systems, more than fifty percent of the microparticles in the flow become trapped. The trapped microparticles are not delivered to the target. For systems that attempt to solve this problem by conveying the fluid at high pressures, the risk of system leakage increases.

In a therapeutic system, to achieve effective treatment, substantially all microparticles introduced into the system should be delivered to the target. Failure to deliver substantially all microparticles to the target reduces the effectiveness of the treatment. Similarly, in a diagnostic system, to achieve an accurate diagnosis, substantially all microparticles introduced into the system should be delivered to the target. Further, for microparticles that constitute a medical device, under delivery of the microparticles to the intended target is an incident reportable to regulatory authorities.

SUMMARY

An apparatus includes a fluid path, a coupling, and a nozzle. The fluid path is to carry a fluid including one or more microparticles. The coupling is located in the fluid path. The nozzle is located in the fluid path to move the fluid through a stagnant region located near the coupling.

An apparatus includes a fluid path and a coupling. The fluid path is to carry a fluid including one or more microparticles. The coupling is located along the fluid path. The fluid path is substantially aligned with a force field.

A method includes introducing a fluid including one or more microparticles into a fluid path including a coupling and aligning the fluid path near the coupling with a force field.

An apparatus includes a coupling including a proximal end and a distal end and a low flow rate fluid path including the coupling to deliver at least about 90% of a source of high density microparticles from the proximal end of the coupling to the distal end of the coupling.

A method includes coupling a source of high density microparticles having high specific activity to a mammal and delivering the high density microparticles having high specific activity to the mammal at a pressure of between about 5 psig and about 30 psig at the source.

A method includes delivering one or more microparticles to a subject, and imaging the one or more microparticles to form image data.

A method includes conveying one or more substantially spherical microparticles to a subject, imaging the one or more substantially spherical microparticles to form image data, and analyzing the image data to identify an anomalous condition.

BRIEF DESCRIPTION OF THE DRAWINGS

FIG. 4 is a flow diagram of a method including coupling a source of high density microparticles having high specific activity to a mammal, and delivering the high density microparticles having high specific activity to the mammal at a pressure of between about 5 psig and about 30 psig at the source in accordance with some embodiments.

FIG. 5 is a Summary Table showing catheter size, pressure ranges, equivalent flow rates, and flush volumes for microparticles suitable for use as the source of microparticles in accordance with some embodiments.

DESCRIPTION

Figure 1A:
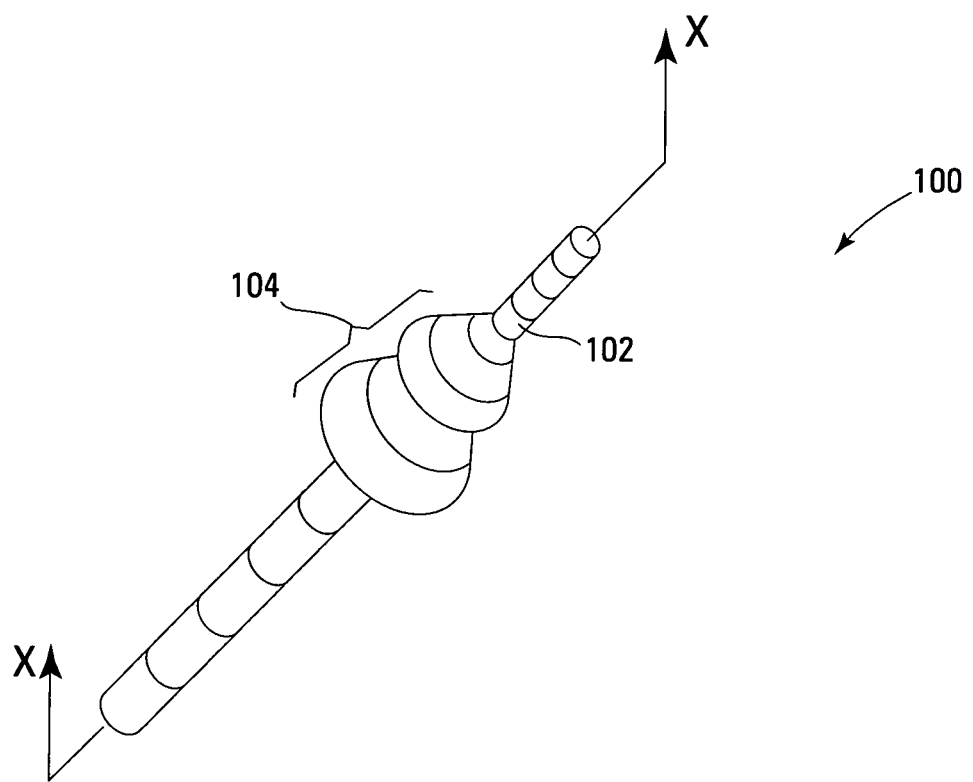
FIG. 1(a) is a perspective view of an apparatus to convey a fluid in accordance with some embodiments.

FIG. 1(a) is a perspective view of an apparatus 100 to convey a fluid in accordance with some embodiments. The apparatus 100 is suitable for use in connection with systems and devices that convey or deliver a fluid. A fluid is a continuous amorphous substance that is readily reshaped and has a tendency to assume the shape of its container. The apparatus 100 is not limited to use in connection with a particular fluid or a particular application or industry. Exemplary fluids suitable for use in connection with the apparatus 100 include liquids and gases. Further embodiments of the apparatus 100 are shown in FIGS. 1(b), 1(c), 2(a), and 2(b) and described below.

Figure 1B:
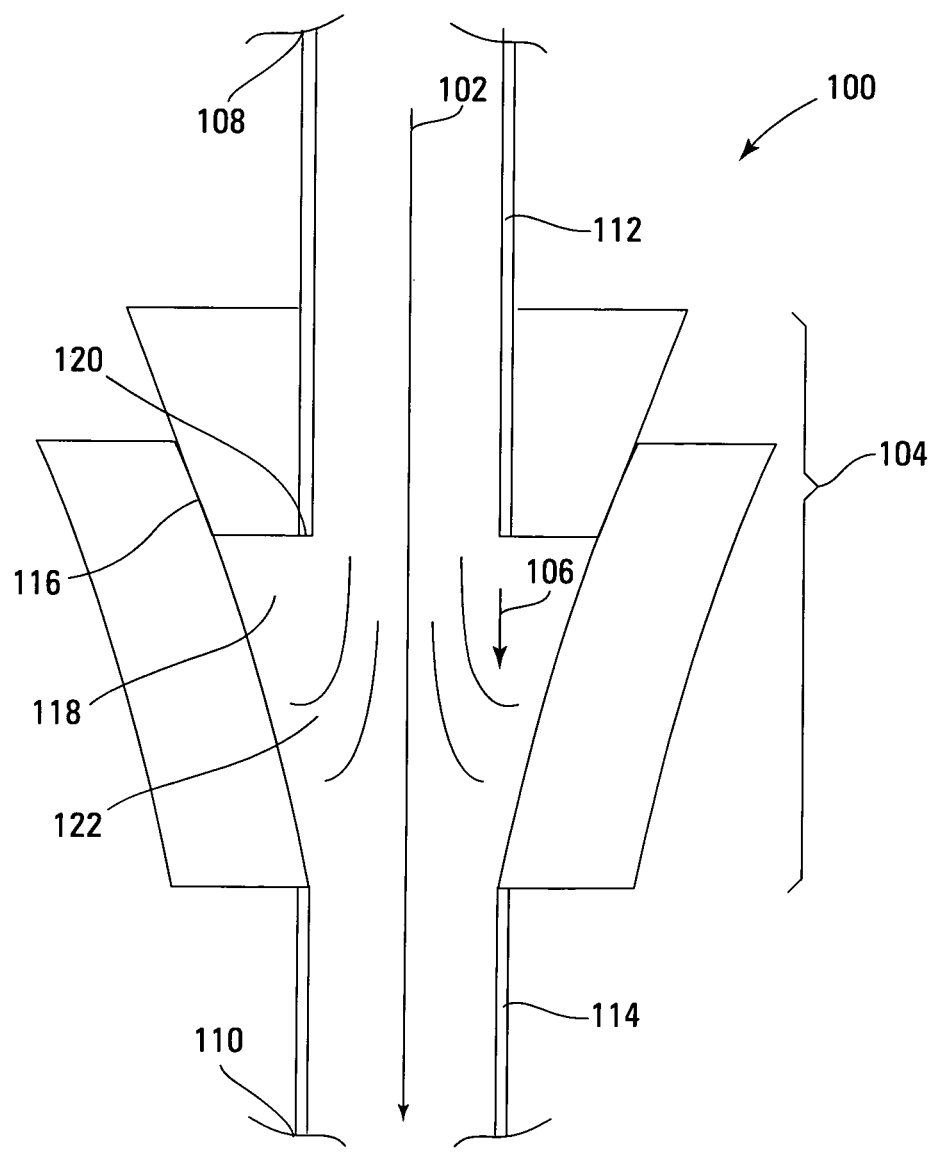
FIG. 1(b) is an illustration of a cross-sectional view at line x-x of the apparatus shown in FIG. 1(a) and including a fluid path and a coupling located in the fluid path and substantially aligned along the field lines of a force field in accordance with some embodiments.

FIG. 1(b) is an illustration of a cross-sectional view at line x-x of the apparatus 100, shown in FIG. 1(a), including a fluid path 102 and a coupling 104 located in the fluid path 102 and substantially aligned along the field lines of a force field 106 in accordance with some embodiments. The fluid path 102 includes a proximal end 108 and a distal end 110 and provides a path or conduit to convey or deliver a fluid from the proximal end 108 to a distal end 110. The delivery of a fluid intravenously for therapeutic use in the treatment of disease is one exemplary application of the apparatus 100. In one illustrative embodiment, the apparatus 100 provides for the delivery of a fluid, such as a fluid including one or more radioactive microparticles, to a human vascular system for the treatment of cancer. Liver cancer is an exemplary disease for which therapies have been developed that can benefit from the use of the apparatus 100. Cancer and other disease states can be diagnosed using microparticle injections. The microvascular bed of cancer lesions, or other diseases, and surrounding healthy tissue can be characterized to allow treatment planning, including but not limited to the number of therapeutic microspheres and the specific activity of the therapeutic microspheres in a subsequent treatment. Other treatments can be planned from the knowledge of the microvascular bed.

In some embodiments, the fluid path 102 is formed from a conduit, such as a tube or microtube. A tube is a conduit that has an inside diameter greater than a few thousand microns. A microtube is a tube that has an inside diameter a between about a fraction of a micron and a few thousand microns. The inside diameter of the conduit is not limited to a particular value. For the transport of a fluid that includes one or more microparticles or microspheres along the fluid path 102, the fluid path 102 is formed from a conduit of sufficient diameter to allow the microparticles to flow unimpeded from the proximal end 108 to the distal end 110. For example, to transport a fluid that includes five micrometer diameter microparticles, in some embodiments the inside diameter of a conduit that forms the fluid path 102 is between about twenty-five micrometers and about fifty micrometers. The conduit can be flexible or inflexible. Exemplary materials suitable for use in connection with the fabrication of the conduit that forms the fluid path 102 include polystyrene, plastic, and metals, such as stainless steel.

The coupling 104 included in the fluid path 102 provides a mechanical connection or link between two or more objects, such as two or more pieces of conduit 112 and 114 or between a conduit and a catheter. A coupling can be formed separately from the objects to be connected or the coupling can be integrated with the objects. The coupling 104 is not limited to a particular type of coupling. Various couplings, connectors, and fittings are suitable for use in forming the coupling 104 in the fluid path 102 of the apparatus 100.

A Luer connector is one type of coupling used as an interconnection component in vascular fluid delivery systems. A Luer connector includes a tapered barrel and a conical male part that fits into the barrel without a seal. In some embodiments, the taper is about six percent. For use in a vascular fluid delivery system, in some embodiments, the apparatus 100 includes a Luer connector for the coupling 104 in the fluid path 102. The coupling material is selected to be compatible with the fluid and the environment and operating conditions, such as temperature and pressure, of the fluid path 102.

In operation, the apparatus 100 conveys a fluid, such as a fluid including one or more microparticles, along the fluid path 102. A microparticle may be spherical but it need not be spherical. Solid or hollow glass or glass composite beads can form microparticles suitable for use in connection with the apparatus 100. In some embodiments, each of the one or more microparticles has a specific gravity of more than about 1.5.

The term microparticle includes nanoparticles, microparticles, and microspheres. Nanoparticles include particles and nanospheres having a diameter of about fifty nanometers to about 1000 nanometers. Microparticles include particles having a diameter of between about 1 μm to about 1000 μm. Microspheres include substantially spherical elements having a diameter between about 1 μm and about 1000 μm. Exemplary materials suitable for use in forming microparticles include inorganic, organic, polymer, radioactive and magnetic materials. Inorganic materials include metals, silica, alumina, titania, glass, and ceramic. Organic materials include polystyrene, melanine, and polylactide. Polymer materials include polyurethane, lignin, polyamide, silicone, copolymers and trimers. A radioactive material exhibits the spontaneous emission of a stream of particles or electromagnetic rays during nuclear decay. The stream may include atomic or subatomic particles that may be charged positively or negatively. Alpha particles and positrons are exemplary positively charged particles. Beta particles are exemplary negatively charged particles. Radioactive materials include radioactive oxides and radioactive polymers. A magnetic material responds to a magnetic field. Magnetic materials include some metals, such as iron, ferromagnetic, and paramagnetic materials. The surface of a microparticle is not limited to being formed from a particular material.

Also, in operation, the fluid path 102 near the coupling 104 is substantially aligned with the force field 106. The fluid path 102 is substantially aligned with the force field 106 when the angle between the direction of travel of microparticles in the fluid path 102 and the direction of the force field 106 is between about thirty-five degrees and about forty-five degrees. The fluid path 102 is very substantially aligned with the force field 106 when the angle between the direction of travel of microparticles in the fluid path 102 and the direction of the force field is less than about thirty-five degrees. When the fluid path 102 is very substantially aligned with the force field 106 fewer of the particles in the fluid path 102 will become trapped than when the fluid path 102 is substantially aligned with the force filed 106. The force field 106 is not limited to a particular type of force field. Exemplary force fields suitable for use in connection with the apparatus 100 include gravitational force fields, magnetic force fields, centrifugal force fields, and electric force fields. The force field 106 can be static or dynamic. A static force field does not vary with time. A dynamic force field varies with time.

The substantial alignment of the fluid path 102 near the coupling 104 with the force field 106 reduces the likelihood of the microparticles being trapped in a gap 116 created in mismatched fittings of the coupling 104. Further, fewer microparticles enter a stagnant fluid region 118 at a re-entrant corner 120, when the fluid path 102 is substantially aligned with the force field 106. Finally, microparticles that enter the stagnant fluid region 118 travel in the direction of the force field 106 into a turbulent region 122 where they are re-entrained or pulled into the fluid flow of the fluid path 102.

Figure 1C:
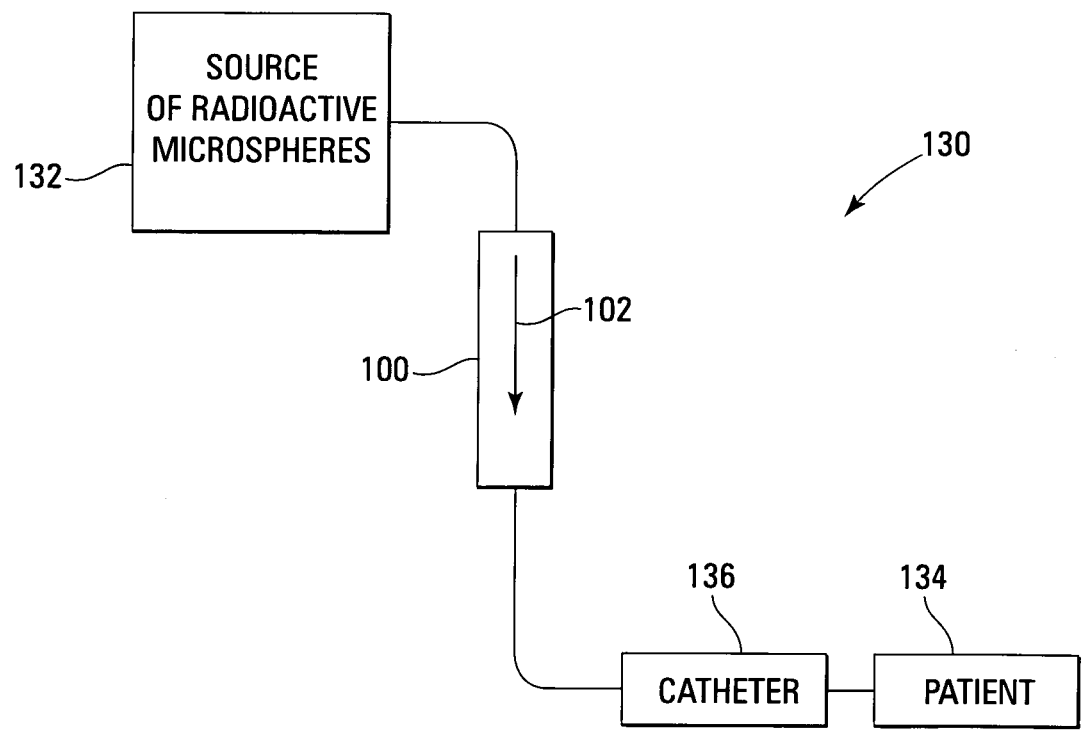
FIG. 1(c) is block diagram of an apparatus including the apparatus shown FIG. 1(a) and coupled to a source of radioactive microparticles and a patient for use in connection with therapies, such as cancer therapies, in accordance with some embodiments.

FIG. 1(c) is block diagram of an apparatus 130 including the apparatus 100, shown FIG. 1(b), coupled to a source of radioactive microparticles 132 and a patient 134 for use in connection with therapies, such as cancer therapies, in accordance with some embodiments. The source of radioactive microparticles 132 includes a container, such as a vial, to hold a fluid including radioactive microparticles. The container is either shielded or maintained in a shielded case to provide protection from the radiation emitted by the radioactive microparticles 132. A catheter 136 can provide a coupling from the fluid path 102 of the apparatus 100 to the patient 134. The catheter 136 is a hollow flexible tube for insertion into a body cavity, duct, or vessel to allow the passage of fluids. In some embodiments, the apparatus 100 is included in the catheter 136.

Figure 1D:
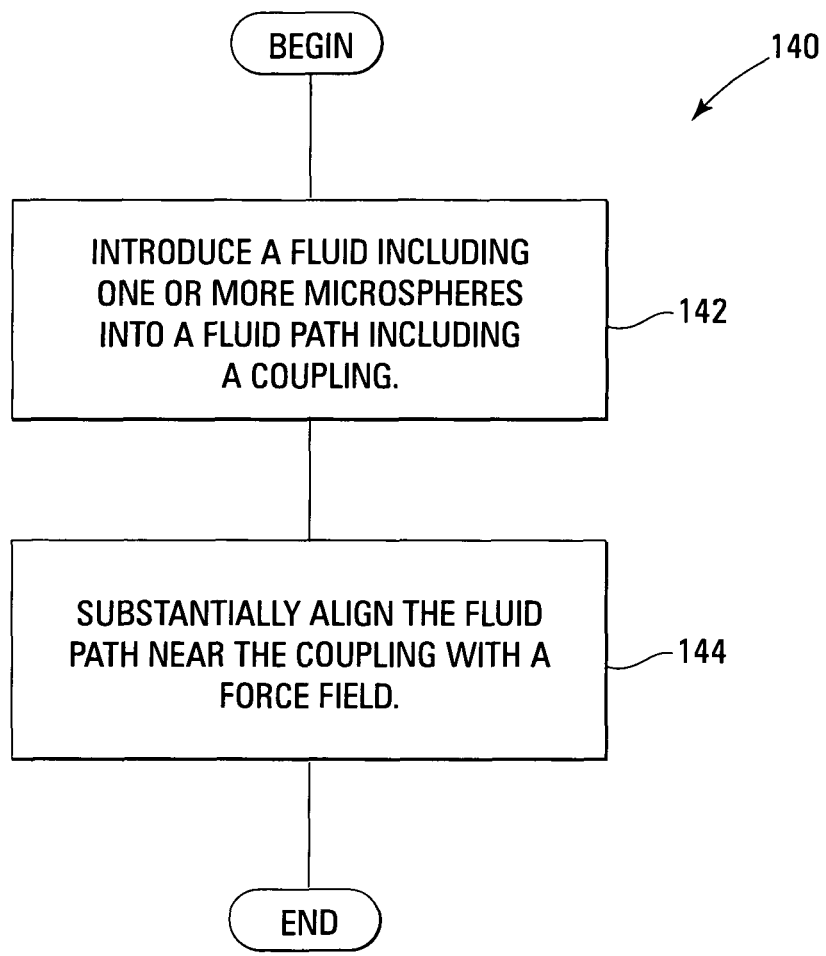
FIG. 1(d) is a flow diagram of a method including introducing a fluid including one or more microparticles into a fluid path including a coupling and substantially aligning the fluid path near the coupling with a force field.

FIG. 1(d) is a flow diagram of a method 140 including introducing a fluid including one or more microparticles into a fluid path including a coupling (block 142), and substantially aligning the fluid path near the coupling with a force field (block 144). In some embodiments, aligning the fluid path near the coupling with the force field includes aligning the fluid path near the coupling with a gravitational field. In some embodiments, the method 140 further includes introducing a cancer patient into the fluid path. And in yet other embodiments, introducing the fluid including one or more microparticles into the fluid path including the coupling includes introducing a slurry of radioactive microparticles under pressure into the fluid path. In some embodiments, the method further includes introducing a flushing fluid having a volume of between about twenty milliliters and about eighty milliliters into the fluid path at an operating pressure of about thirty pounds per square inch per square inch gauge.

Figure 2A:
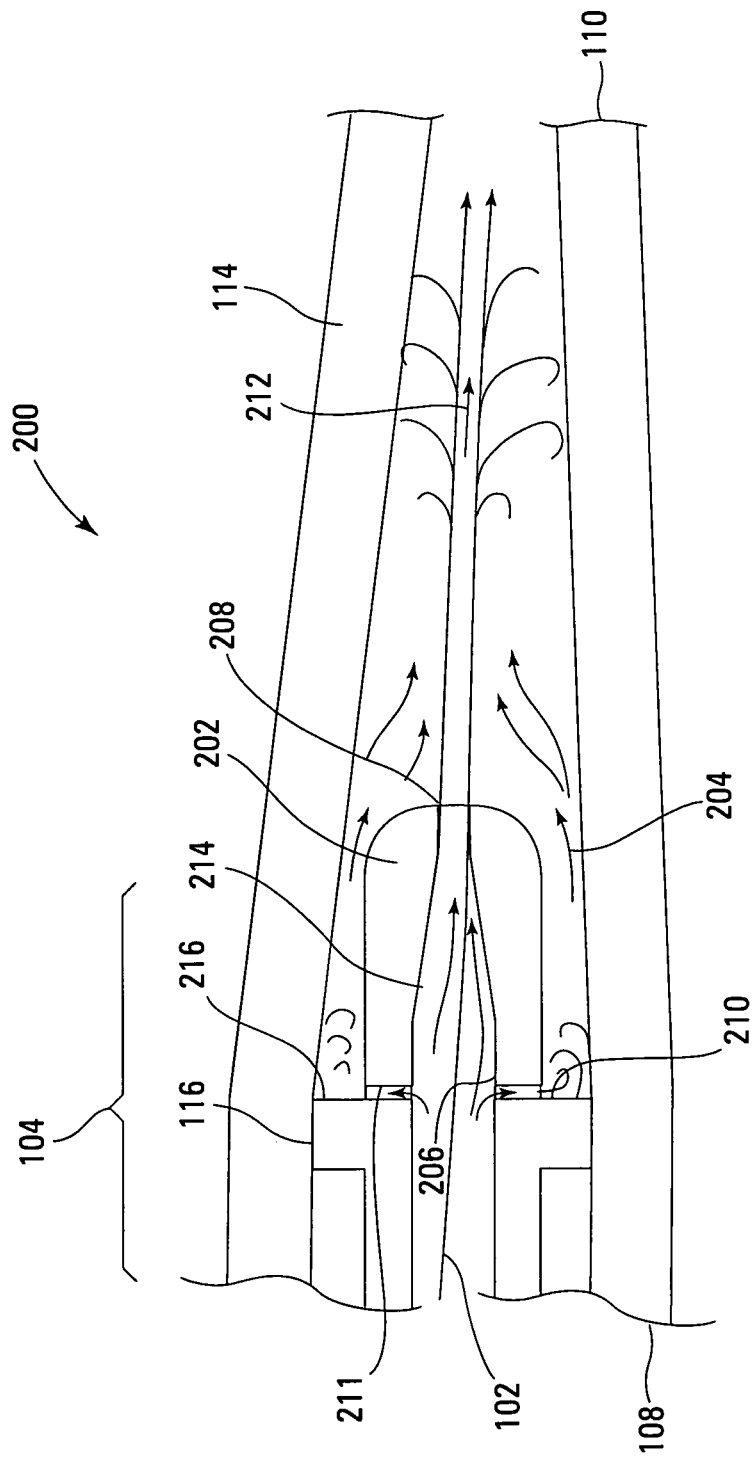
FIG. 2(a) is an illustration of a cross-sectional view of an apparatus including the fluid path shown in FIG. 1(a), the coupling shown in FIG. 1(a) and located in the fluid path shown in FIG. 1(a), and a nozzle located in the fluid path to move a fluid through a stagnant region located near the coupling in accordance with some embodiments.

FIG. 2(a) is an illustration of a cross-sectional view of an apparatus 200 including the fluid path 102, shown in FIG. 1(a), the coupling 104, shown in FIG. 1(a), located in the fluid path 102, and a nozzle 202 located in the fluid path 102 to move a fluid through a stagnant region 204 located near the coupling 104. The nozzle 202 includes an input port 206 and an output port 208. In some embodiments, the nozzle 202 includes a side port 210. The nozzle 202 is not limited to a particular number of side ports. In some embodiments, the nozzle 202 includes the side port 210 and one or more additional side ports, such as side port 211.

The fluid path 102 includes the proximal end 108, shown in FIG. 1(b), and the distal end 110, shown in FIG. 1(b), and provides a path or conduit to convey or deliver a fluid from the proximal end 108 to the distal end 110. The delivery of a fluid intravenously for therapeutic use in the treatment of disease is one exemplary application of the apparatus 200. In one illustrative embodiment, the apparatus 200 provides for the delivery of a fluid, such as a fluid including one or more radioactive microparticles, to a human vascular system for the treatment of cancer. Liver cancer is an exemplary disease for which therapies have been developed that can benefit from the use of the apparatus 200.

In operation, all microparticles that enter the fluid path 102 at the proximal end 108 of the apparatus 200 should enter the nozzle 202 at the input port 206 and should exit the apparatus 200 at the distal end 110. The stagnant region 204 is an interior area of the coupling 104 in which microparticles entering the coupling 104 at the input port 206 of the nozzle 202 can become trapped. When microparticles become trapped in the stagnant region 204 they do not pass through the coupling 104 to the distal end 110. In some systems, such as therapeutic systems, it is desirable to keep the number of trapped microparticles low.

Introduction of the nozzle 202 into the fluid path 102 changes the dynamics of the fluid flow in the coupling 104. In some embodiments, the input port 206 of the nozzle 202 has an input port cross-sectional area and the output port 208 has an output port cross-sectional area. Making the cross-sectional area of the input port 206 greater than the cross-sectional area of the output port 208 reduces the likelihood that microparticles traveling along the fluid path 102 will become trapped in the stagnant region 204. In some embodiments, the output port 208 has a diameter of between about 0.2 millimeters and about 1 millimeter. In some embodiments, the output port 208 cross-sectional area is about forty percent of the input port 206 cross-sectional area. In some embodiment, the output port 208 diameter is equal to between about five microparticle and about ten microparticle diameters. In addition, making the cross-sectional area of the input port greater than the cross-sectional area of the output port forces fluid flow through the side port 210 to assist in moving microparticles through the stagnant region 204.

The velocity of the fluid at the output port 208 of the nozzle 202 creates a low pressure region to draw fluid and microparticles from the stagnant region 204 into the fluid path 102. Further, the nozzle 202 occupies a volume in the coupling 104 which increases the flow rate and entrainment of microparticles into the fluid path 102 near the nozzle 202. In addition, positioning the output port 208 of the nozzle 202 beyond the stagnant region 204 results in delivery of substantially all microparticles in the fluid to a location in the coupling 104 beyond the stagnant region 204.

The nozzle 202 includes a nozzle fluid path 212 located between the input port 206 and the output port 208. In some embodiments, the nozzle fluid path 212 includes a taper 214. In some embodiments, the slope of the taper 214 is less than about forty-five degrees. The slope of the taper 214 is the largest slope of the curve of the nozzle fluid path 212 between the input port 206 and the output port 208. For the taper 214 having a slope of less than about forty-five degrees, the likelihood of microparticle bridging along the nozzle fluid path 212 is reduced. Microparticle bridging occurs when a group of microparticles block or partially block the nozzle fluid path 212.

In some embodiments, the nozzle 202 includes the side port 210. The side port 210 is an opening located on a side surface of the nozzle 202. Introduction of the side port 210 into the nozzle 202 changes the dynamics of the fluid flow in the coupling 104. The side port 210 provides a fluid path through the stagnant region 204 for a fluid entering the nozzle 202 at the input port 206. The side port 210 is located near the input port 206 of the nozzle 202. Further, as described above, making the cross-sectional area of the input port 206 greater than the cross-sectional area of the output port 208 creates a back pressure to force more fluid flow through the side port 210. The fluid flow at the side port 210 induces turbulence near the nozzle 202 that sweeps microparticles from the stagnant region 204 near the nozzle 202 into the fluid path 102. The fluid flow provided by the side port 210 to the stagnant region 204 removes substantially all microparticles from the stagnant region 204.

The side port 210 is not limited to a particular shape. In some embodiments, the side port 210 is substantially a cylindrical passage that has a diameter at least as large as the largest microparticle. However, to reduce the likelihood of blockage by bridging, the side port diameter should be at least two or more microparticle diameters. In some embodiments, the side port diameter is about 0.25 millimeters.

The nozzle 202 is not limited to a particular number of side ports. The side port 210 can be replicated along the perimeter of the nozzle 202. The replication of the side port 210 is not limited to a particular configuration. In some embodiments, the side port 210 includes two or more side ports spaced a substantially equal distance from each other along the perimeter of the nozzle 202. In some embodiments, the side port 210 includes four side ports with each of the four side ports spaced a substantially equal distance from each other along the perimeter of the nozzle 202.

In some embodiments, the nozzle 202 includes a nozzle flange 216. The nozzle flange 216 is sized and centered in the coupling 104 to form a seal at the leading edge of the nozzle flange 216. The purpose of the seal between the nozzle flange 216 and the coupling 104 is to substantially prevent formation of the gap 116. Preventing formation of the gap 116 reduces the number of potential sites that can trap microparticles in the coupling 104.

In operation, a fluid enters the apparatus 200 at the proximal end 108 and flows along the fluid path 102 through the coupling 104 and the nozzle 202 and exits the coupling 104 at the distal end 110. For a fluid that includes one or more microparticles, the coupling 104 and the nozzle 202 provide a fluid flow that keeps the number of microparticles trapped in regions of the coupling 104, such as the stagnant region 204, low.

Figure 2B:
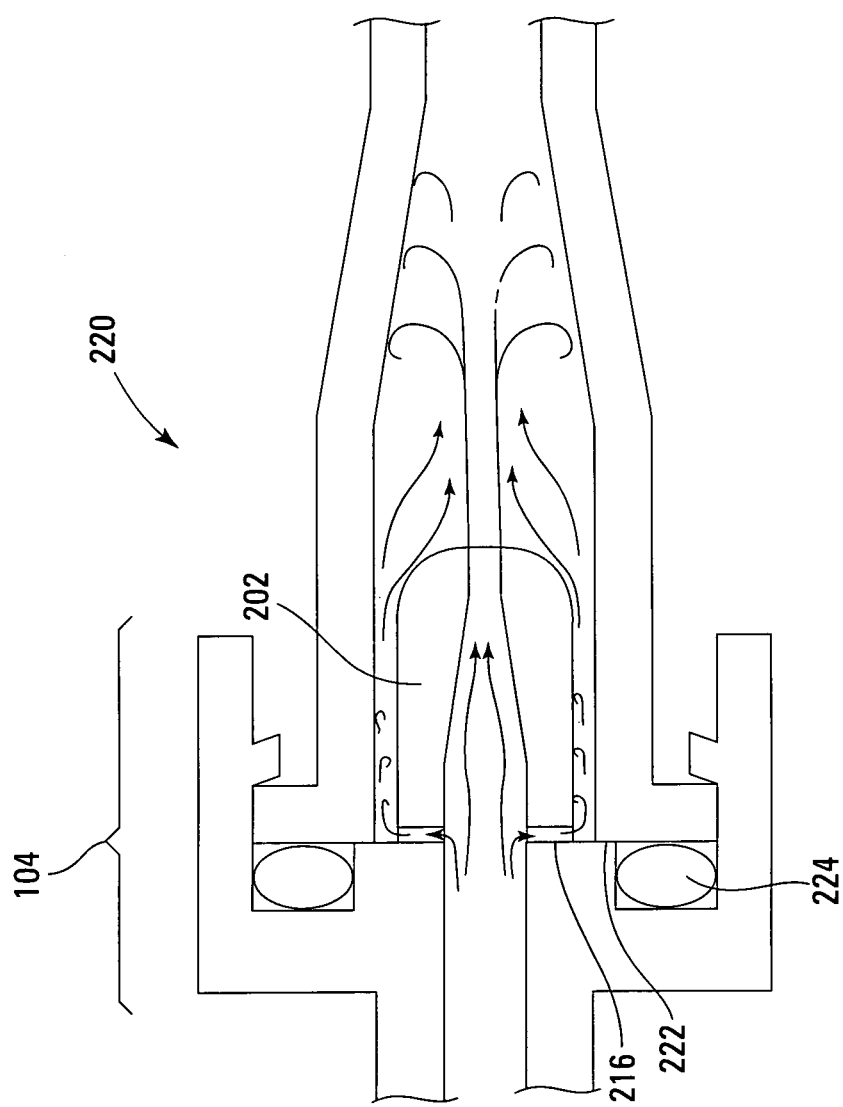
FIG. 2(b) is a detailed illustration of an apparatus including the coupling shown in FIG. 2(a), the nozzle, shown in FIG. 2(a), and a flat-face seal and an elastomeric seal in accordance with some embodiments.

FIG. 2(b) is a detailed illustration of an apparatus 220 including the coupling 104, shown in FIG. 2(a), the nozzle 202, shown in FIG. 2(a), and a flat-face seal 222 and an elastomeric seal 224 in accordance with some embodiments. In some embodiments, the nozzle 202 includes the nozzle flange 216. The flat-face seal 222 is formed between in the coupling 104 and the nozzle flange 216. A flat-face seal includes a surface-to-surface seal between the two components. In some embodiments, the coupling 104 includes the elastomeric seal 224. The elastomeric seal 224 is formed by a ring of elastomeric material compressed between the two components of the coupling 104.

The apparatus 200, shown in FIG. 2(a) and the apparatus 220 shown in FIG. 2(b) can be included in a fluid delivery system coupled to a patient. In such embodiments, each of the apparatus 200 and 220 enables effective infusions of high density, high potency microparticles at low infusion pressure and flow rates. The low infusion pressure reduces the likelihood of leakage. The low flow rate reduces the possibility of reflux (back flow into a patient's vasculature) which in turn increases the likelihood that the microparticles will be delivered to the target.

Figure 3:
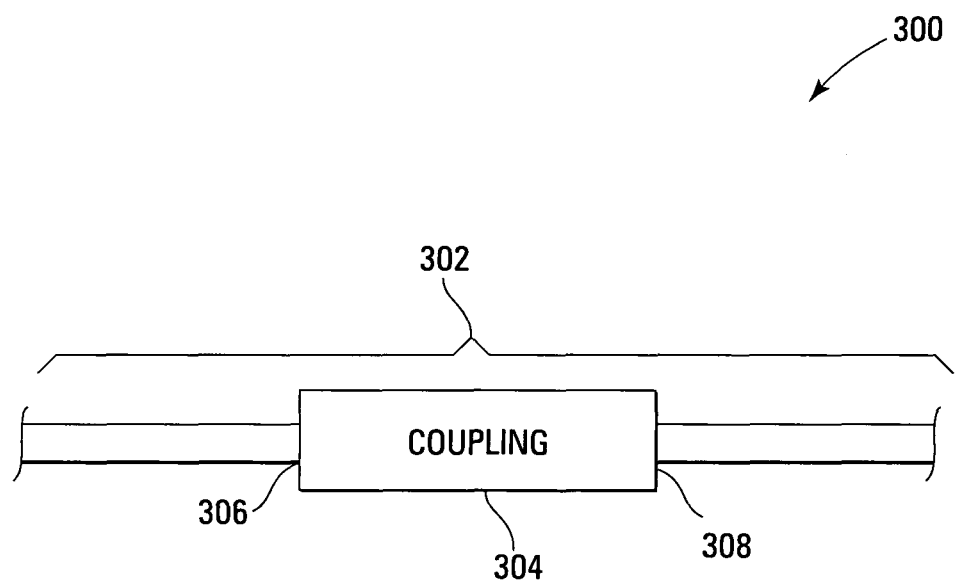
FIG. 3 is an illustration of apparatus including a low flow rate fluid path including a coupling in accordance with some embodiments.

FIG. 3 is an illustration of apparatus 300 including a low flow rate fluid path 302 including a coupling 304 in accordance with some embodiments. The coupling 304 has a proximal end 306 and a distal end 308. In operation, the low flow rate fluid path 302 including the coupling 304 delivers at least about 90% of a source of high density microparticles from the proximal end 306 to the distal end 308 of the coupling 304. For example, if a source of high density microparticles includes ten million particles, then in operation the apparatus 300 delivers at least about nine million high density microparticles from the source to the distal end 308 of the coupling 304. A catheter is an exemplary coupling suitable for use in connection with the apparatus 300. In some embodiments, in operation, the low flow rate fluid path 302 has a flow rate of between about 0.05 milliliters per second and about 0.93 milliliters per second. A high density microparticle has a specific gravity of greater than about 1.5. A high specific activity radioactive microparticle has a specific activity of greater than about 0.5 Ci/g. For non-radioactive particles, high specific activity refers to the concentration of active ingredient, for example, a therapeutic drug or enhancing drug such as an oxidizing agent. The apparatus 300 improves microparticle delivery to a target and is particularly useful when the volume in the coupling 304 available to trap microparticles exceeds about 5% of the volume of the microparticles intended for delivery to the target.

FIG. 4 is a flow diagram of a method 400 including coupling a source of high density microparticles having high specific activity to a mammal (block 402), and delivering the high density microparticles having high specific activity to the mammal at a pressure of between about 5 psig and about 30 psig at the source (block 404). In some embodiments, coupling the source of high density microparticles having high specific activity to the mammal includes connecting a catheter between the source and the mammal. In some embodiments, delivering the high density microparticles having high specific activity to the mammal at the pressure of between about 5 psig and about 30 psig at the source includes delivering more than about 90% of the high density microparticles available at the source to the mammal.

FIG. 5 is a Summary Table showing catheter size, pressure ranges, equivalent flow rates, and flush volumes for microparticles suitable for use as the source of microparticles in accordance with some embodiments. As can be seen in the Summary Table, for a catheter size of 3 French, the pressure range in the fluid path 302, shown in FIG. 4, is between about 5 psig and about 30 psgi. The equivalent flow is 0.49±0.44 mL/s and the flush volume is less than about 60 ml. For a catheter size of 5 French, the pressure range in the fluid path 302, shown in FIG. 4, is between about 5 psig and about 30 psig. The equivalent flow is 2.1±0.9 and the flush volume is less than about 60 ml. The flow rate variability is based on three standard deviations. Flow rate values for 4 French catheters fall between the 3 and 5 French values. At the pressures and flow rates for the fluid path shown in the Summary Table, a source of high density microparticles can include a seal rated for a lower pressure than for higher pressure fluid paths.

Figure 6:
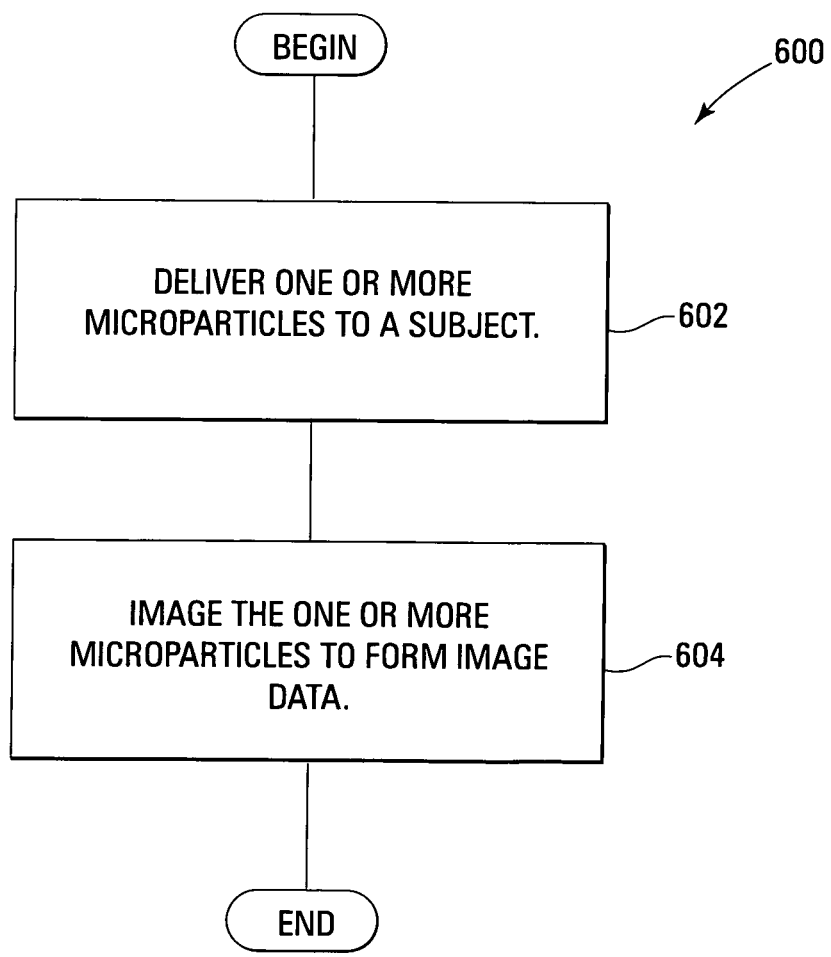
FIG. 6 is a flow diagram of a diagnostic method in accordance with some embodiments.

FIG. 6 is a flow diagram of a diagnostic method 600 in accordance with some embodiments. The method 600 includes delivering one or more microparticles to a subject (block 602), and imaging the one or more microparticles to form image data (block 604). The image data can be analyzed by a physician, clinician, or a computing system to generate a diagnosis. The image data is not limited to a particular type of data. Exemplary types of data include digital, such as digital data stored in a computing system, analog, such as photographs or other displayable images, and mixed digital and analog. In some embodiments, delivering the one or more microparticles to the subject includes delivering the one or more microparticles to a microvascular bed. A microvascular bed includes the small vascular structures in organs, such as the human liver. These small vascular structures can trap substantially spherical microparticles. In some embodiments, delivering the one or more microparticles to the subject includes delivering one or more radioactive microparticles to the subject. In some embodiments, delivering the one or more microparticles to the microvascular bed includes delivering the one or more microparticles to the microvascular bed in a human liver or other human organ. In some embodiments, delivering the one or more microparticles to the microvascular bed includes delivering one or more radioactive microparticles to the microvascular bed in a human liver, breast, brain, or other human organ. The imaging of the microparticles is not limited to a particular method. Any method of imaging capable of detecting microparticles or clusters of microparticles is suitable for use in connection with the method 600. Exemplary imaging methods include ultrasound, magnetic resonance imaging, and computer aided tomography.

Figure 7:
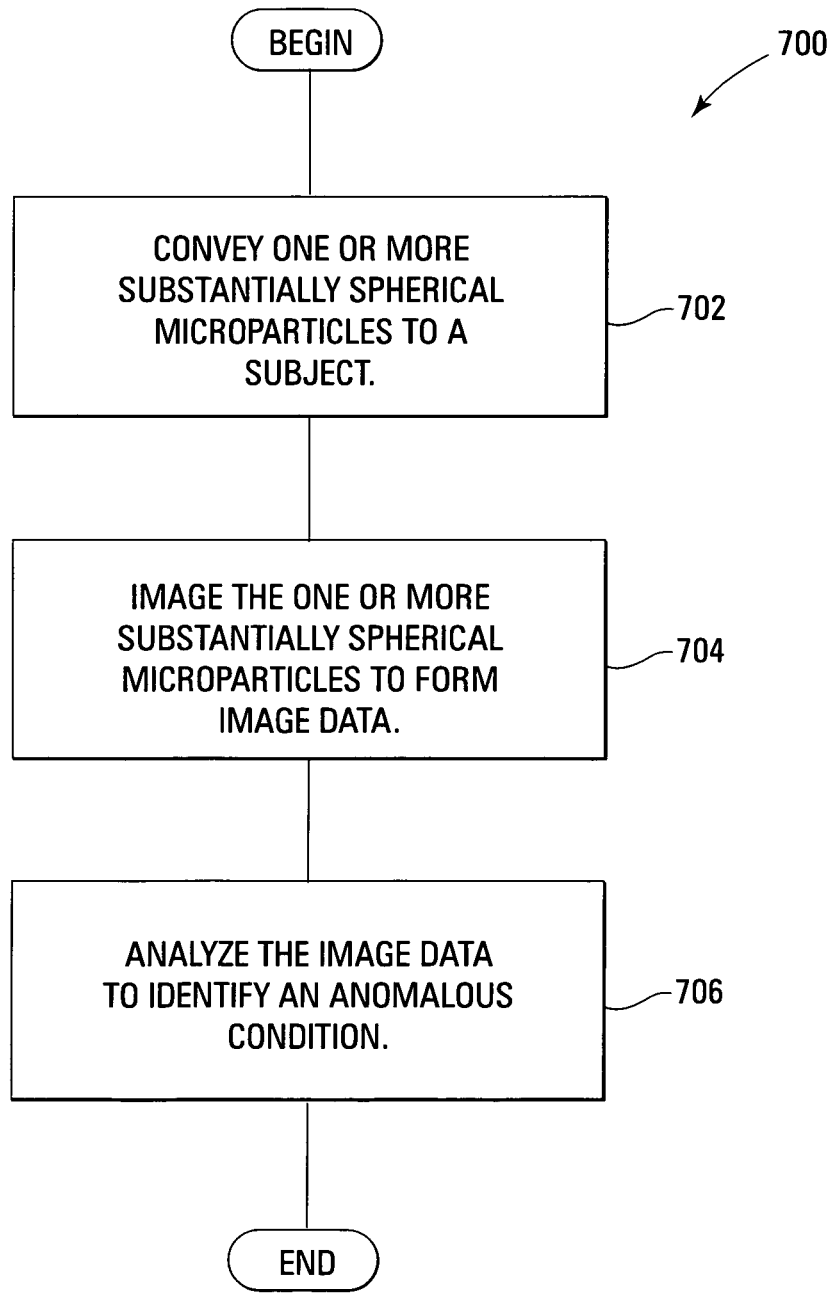
FIG. 7 is a flow diagram of a diagnostic method including analysis in accordance with some embodiments.

FIG. 7 is a flow diagram of a diagnostic method 700 including analysis in accordance with some embodiments. The method 700 includes conveying one or more substantially spherical microparticles to a subject (block 702), imaging the one or more substantially spherical microparticles to form image data (block 704), and analyzing the image data to identify an anomalous condition (block 706). Cancer is one example of an anomalous condition that can be detected and analyzed using the method 700. The method 700 also includes delivering a small numbers of radiocative microparticles a subject, such as an animal, analyzing the location and distribution of the microparticles in the subject, and a generating a treatment regime from the analysis. The treatment regime can include delivering a larger number of substantially spherical microparticles to the subject. In some embodiments, conveying the one or more substantially spherical microparticles to a subject includes conveying one or more radioactive microparticles to the subject. In some embodiments, analyzing the image data to identify the anomalous condition includes comparing the image data against data that identifies known diseases to identify a an animal disease state. In some embodiments, imaging the one or more substantially spherical microparticles to form image data includes imaging using a magnetic resonance imaging system. However, the methods of imaging are not limited to a particular method. Any imaging method capable of detecting microparticles can be used in connection with the described diagnostic methods. Exemplary imaging systems include systems that image using waves, such as electromagnetic or acoustic waves. Exemplary imaging systems that use electromagnetic waves include magnetic resonance imaging and computer aided tomography. Exemplary imaging systems that use acoustic waves include ultrasound imaging systems.

Although many alterations and modifications of the described embodiments will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims.

What is claimed is:

1. A microparticle delivery apparatus for delivering one or more microparticles to a patient, the apparatus comprising:
a fluid path having a fluid flow of a fluid including the one or more microparticles;

a coupling located in the fluid path; and a nozzle located in the fluid path to move the fluid through a stagnant region positioned radially outward of the nozzle, the nozzle including an input port at an upstream end thereof and an output port at a most downstream end thereof defining a central fluid path through the nozzle from the input port to the output port, the nozzle further including one or more side ports positioned near the input port of the nozzle, the one or more side ports defining at least one additional fluid path through the nozzle, wherein the fluid flow flows into the nozzle via the input port, a first portion of the fluid flow that flows into the nozzle via the input port flows through the central fluid path and out of the nozzle via the output port and into the fluid path, and a second portion of the fluid flow that flows into the nozzle via the input port flows through the one or more side ports and moves the fluid through the stagnant region and into the fluid path while bypassing the central fluid path of the nozzle.

2. The apparatus of claim 1, wherein the input port has an input port cross-sectional area and the output port has an output port cross-sectional area, the input port cross-sectional area being greater than the output port cross-sectional area.

3. The apparatus of claim 2, wherein the nozzle includes a nozzle fluid path from the input port to the output port that includes a taper.

4. The apparatus of claim 3, wherein the taper has a slope of less than about forty-five degrees.

5. The apparatus of claim 1, wherein the nozzle includes a flanged fitting substantially centered in the coupling and sized to form a seal to substantially prevent back flow.

6. The apparatus of claim 5, wherein the seal includes an elastomeric seal.

7. The apparatus of claim 5, wherein the seal includes a flange forming a flat-face seal.

8. The apparatus of claim 1, wherein the coupling includes a seal.

9. The apparatus of claim 1, wherein the coupling includes a tapered fitting.

10. A microparticle delivery apparatus for delivering one or more microparticles to a patient, the apparatus comprising:

a fluid path having a fluid flow of a fluid including the one or more microparticles;

a coupling located in the fluid path; and a nozzle located in the fluid path to move the fluid through a stagnant region positioned radially outward of the nozzle, the nozzle having a longitudinal axis and including an input port at an upstream end thereof and an output port at a most downstream end thereof defining a central fluid path through the nozzle from the input port to the output port, wherein at least a portion of the input port and at least a portion of the output port are in-line with the longitudinal axis of the nozzle, the nozzle further including one or more side ports positioned near the input port of the nozzle, the one or more side ports defining at least one additional fluid path through the nozzle, wherein the fluid flow flows into the nozzle via the input port, a first portion of the fluid flow that flows into the nozzle via the input port flows through the central fluid path and out of the nozzle via the output port and into the fluid path, and a second portion of the fluid flow that flows into the nozzle via the input port flows through the one or more side ports and moves the fluid through the stagnant region and into the fluid path while bypassing the central fluid path of the nozzle.

* * * * *